United States Patent

Sandock et al.

Patent Number: 5,827,280
Date of Patent: Oct. 27, 1998

[54] DEVICE FOR LOCKING A PROTECTIVE ENDOSCOPIC ELECTRODE SLEEVE

[75] Inventors: Paul Sandock, New Hartford; Lauren Young, Poland, both of N.Y.

[73] Assignee: ConMed Corporation, Utica, N.Y.

[21] Appl. No.: 618,205

[22] Filed: Mar. 19, 1996

[51] Int. Cl.⁶ .................................................. A61B 17/36
[52] U.S. Cl. ................................................................ 606/46
[58] Field of Search ........................... 600/106, 121, 600/124, 125; 606/46–48

[56] References Cited

U.S. PATENT DOCUMENTS

| | | |
|---|---|---|
| 4,936,842 | 6/1990 | D'Amelio et al. . |
| 5,084,043 | 1/1992 | Hertzmann et al. ..................... 606/3 |
| 5,154,164 | 10/1992 | Chikama ................................ 600/125 |
| 5,174,300 | 12/1992 | Bales et al. . |
| 5,197,963 | 3/1993 | Parins ..................................... 606/48 |
| 5,219,348 | 6/1993 | Buess et al. . |
| 5,273,524 | 12/1993 | Fox et al. . |
| 5,295,956 | 3/1994 | Bales et al. . |
| 5,429,596 | 7/1995 | Arias et al. . |
| 5,439,005 | 8/1995 | Vaughn . |
| 5,468,240 | 11/1995 | Gentelia et al. . |
| 5,556,367 | 9/1996 | Yabe et al. ............................. 600/121 |

FOREIGN PATENT DOCUMENTS 4-361731  12/1992  Japan ..................................... 600/121

*Primary Examiner*—William E. Kamm
*Assistant Examiner*—George R. Evanisko
*Attorney, Agent, or Firm*—Larson & Taylor

[57] ABSTRACT

A locking device for a protective sleeve of an endoscopic electrode assembly having a connector for connecting the electrode assembly to a control handle, wherein the locking device comprises a post extending longitudinally from the connector and surrounding the elongated electrode, and a sleeve grip connected to the proximal end of the protective sleeve, surrounding the post. The sleeve grip has an unlocked position wherein the sleeve grip is movable longitudinally with respect to the post and a locked position wherein the sleeve grip is restricted from moving longitudinally with respect to the post.

7 Claims, 4 Drawing Sheets

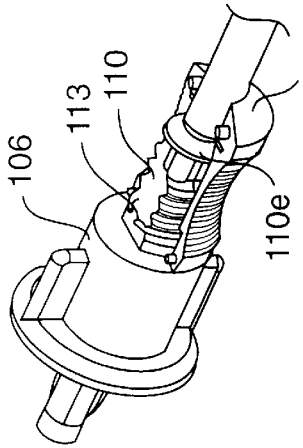
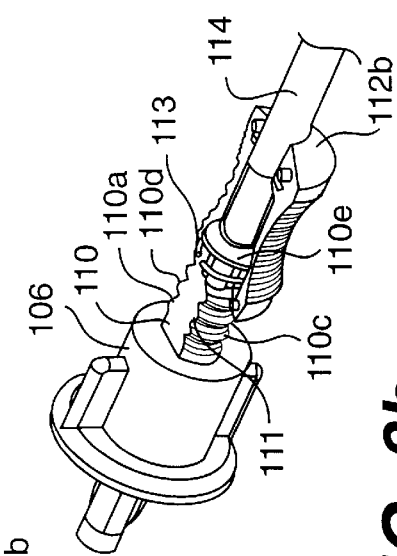
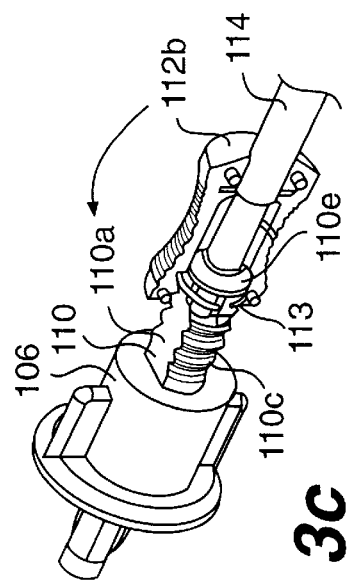
FIG. 3a
FIG. 3b
FIG. 3c

DEVICE FOR LOCKING A PROTECTIVE ENDOSCOPIC ELECTRODE SLEEVE

BACKGROUND OF THE INVENTION

1. Field of the Invention

The present invention relates generally to electrosurgical instruments, and more particularly to a reliable, inexpensive, safe, and efficient device for locking a protective endoscopic electrode sleeve on an electrosurgical instrument having suction and irrigation capabilities for use during endoscopic procedures.

2. Prior Art

Typically, during electrosurgery, an electrosurgical generator provides a high frequency or radio frequency signal to a hand-held surgical electrode having a thin knife-like tip which is applied to a patient. The patient is grounded to the generator via a patient ground plate. The relatively small area of contact by the electrode with the patient provides an intense current in a highly localized area, producing a cutting action. This current then passes through the patient's body to the patient ground plate wherein the area of contact is large enough that no burning effect occurs at this location.

For use during endoscopic surgery electrosurgical instruments typically are provided with elongated electrodes which are attached to control handles which provide current to the electrodes. The elongated electrodes are directed through an appropriately sized trocar tube. An electrosurgical instrument of this type is shown in copending U.S. patent application Ser. No. 08/608,330, to the same inventor herein, entitled Electrosurgical Suction/Irrigation Instrument, filed Feb. 28, 1996, which is now U.S. Pat. No. 5,609,573, issued Mar. 11, 1997, and is incorporated herein by reference.

In these types of instruments, it is well known in the art to provide suction and irrigation capabilities in addition to the electrosurgical therapeutic current capabilities so that several functions may be provided through one trocar tube. Also, these types of instruments can be difficult to accurately control because the electrode tip is located at the end of an elongated device. Therefore, the endoscopic electrodes currently on the market are available with and without protective sheaths or sleeves that advance and retract to cover the electrode's surgical tip. The purpose of such a protective sleeve is to allow the surgeon to cover the electrosurgical tip when using suction and irrigation, when using the instrument for retraction, or otherwise using the instrument for purpose other than electrosurgery. These electrosurgical tips generally consist of formed wire of various shapes including but not limited to "L" shapes, "J" shapes and needles. As such, these wires have the potential to damage underlying tissue and/or organs particularly during tasks where the tip is not directly visible to the surgeon. An example of this potentially dangerous situation would be during aspiration of pools of liquid that are not transparent (which tends to be the case) because the typical instrument tip must be completely submerged to effectively aspirate. As a result of this potential for damage, manufacturers started providing extendable and retractable sleeves that isolated the electrosurgical tip from coming in contact with surrounding tissue.

During surgical tasks that are better performed with the protective sleeve extended, it is not desirable for this sleeve to retract inadvertently and expose the surgical tip. An object of the present invention is to avoid inadvertent retraction of the protective sleeve during manipulation of the instrument when the tip is pushed into an anatomical structure creating an axial force in the retracting direction. If sufficient, this force can retract the sleeve until the electrosurgical tip makes contact with the structure.

Another object of the present invention is to avoid inadvertent retraction of the protective sleeve during manipulation of the instrument when the locking sleeve grip at the proximal end of the electrode "bottoms out" on top of the trocar cannula creating an axial force in the retracting direction. If sufficient, this force can retract the sleeve, fully exposing the electrosurgical tip.

A further object of the present invention is to avoid inadvertent retraction of the protective sleeve during a typical surgical procedure when the electrode is inserted through a trocar cannula which allows access to the surgical site. During manipulation of the instrument in the axial direction there is mechanical drag on the electrode protective sleeve caused by internal components (such as seals, doors, etc.) of the trocar cannula. As a result, if sufficient drag exists, the electrode protective sleeve can be inadvertently retracted simply by moving the instrument axially within the trocar cannula.

Other objects and many of the attendant advantages of the present invention will become apparent upon consideration of the following detailed description of illustrated embodiments of the invention.

SUMMARY OF THE INVENTION

In accordance with the present invention, an effective, safe, reliable and efficient device is provided for locking a protective sleeve in an extended position over an electrode of an endoscopic electrosurgical device.

A connector which connects the electrode assembly to a control handle of an electrosurgical instrument is provided with a post extending longitudinally and distally therefrom and surrounding the electrode, and a sleeve grip connected to the proximal end of the sleeve, the sleeve grip surrounding said post and having an unlocked position wherein the sleeve grip is movable longitudinally with respect to the post and a locked position wherein the sleeve grip is restricted from moving longitudinally with respect to the post.

In a preferred embodiment the post is flat on two opposite sides such that it has a minor diameter equal to the distance between the two flat sides and a major diameter equal to the distance between the two remaining portions. A relief portion is provided at the proximal end of the post such that, in this relief portion, only one small portion of the post has a diameter equal to the major diameter. The sleeve grip has an axial hole therethrough at the distal end for retaining the proximal end of a protective sleeve. The proximal end of the sleeve grip has an axial hole for accepting the post of the connector and as the sleeve grip is moved longitudinally with respect to the post. The protective sleeve is thus moved longitudinally with respect to the connector, and therefore, with respect to the cannula and the electrode. The diametrical shape of the hole through the sleeve grip closely matches the diametrical shape of the post such that the sleeve grip will slide longitudinally over the post only when in one particular rotational orientation. When the sleeve grip is in the extended position, it may be rotated around the relief portion of the post such that the minor diameter of the hole in the sleeve grip aligns with the major diameter of the post, thus preventing the sleeve grip from being urged proximally along the post. In this manner the protective sleeve may be locked in a position which conceals the electrode.

Thus, in this embodiment of the invention, locking is achieved by fully advancing the locking sleeve grip forward towards the distal end and turning the locking sleeve grip one-quarter turn in the clockwise direction (as viewed down the axis of the instrument from the proximal end). In this position, the locking sleeve grip, and as a result, the protective sleeve, cannot be slid back to the retracted position. To retract the protective sleeve from this position, the user must first turn the locking sleeve grip counterclockwise one-quarter turn. The user always has the option of advancing the locking sleeve grip but not turning it into the locked position.

Further, a detent mechanism is provided for retaining the sleeve grip. Thus, the sleeve grip, and therefore the protective sleeve, may be retained in any of several longitudinal positions with respect to the electrode.

BRIEF DESCRIPTION OF THE DRAWINGS

FIG. 3a is a cutaway view exposing the same embodiment of locking device of the present invention in the retracted position.

FIG. 3b is a cutaway view exposing the same embodiment of the locking device of the present invention in the extended but unlocked position.

FIG. 3c is a cutaway view exposing the same embodiment of the locking device of the present invention in the extended position and rotated 90° relative to that position shown in FIG. 3b so as to depict the locking device in the locked position.

DETAILED DESCRIPTION OF THE PREFERRED EMBODIMENTS

Figure 1:
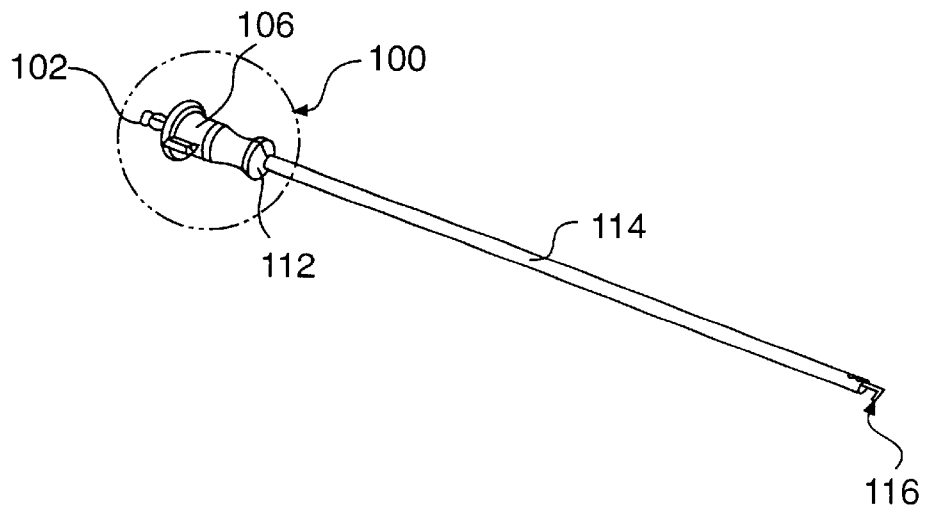
FIG. 1 is a perspective view of an electrode assembly having a preferred embodiment of the device of the present invention in the retracted position such that the electrode tip is exposed.

With reference now to the drawings, in which like numerals represent like elements throughout the several views, FIG. 1 is a perspective view of a electrode assembly having a preferred embodiment of the locking device of the present invention. Assembly 100 is shown with a sleeve grip 112 in the retracted position with respect to connector 106, thereby exposing an electrode tip 116 beyond the protective sleeve 114.

Figure 2:
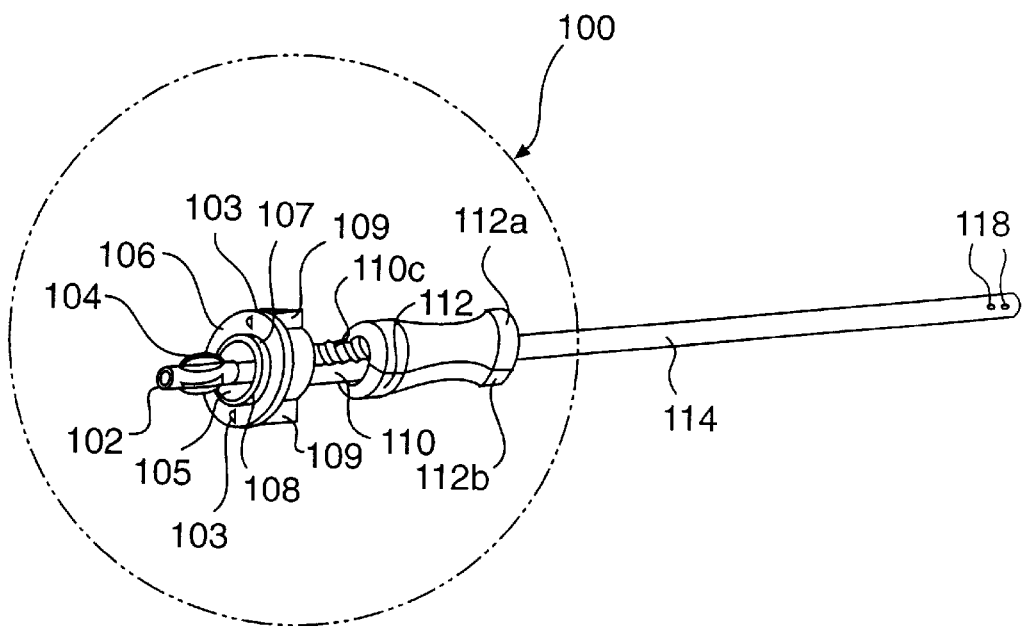
FIG. 2 is a perspective view of an electrode assembly having the embodiment of the device of the present invention shown in FIG. 1, in the extended position such that the electrode tip is covered by the protective sleeve.

FIG. 2 is a more detailed view of the electrode assembly 100 in FIG. 1 with sleeve grip 112 in the extended position with respect to connector 106, thereby covering electrode tip 116 with protective sleeve 114. Electrode assembly 100 is shown having a stainless steel cannula 102 running longitudinally therethrough with electrode tip 116 being rigidly and electrically connected to cannula 102 at the distal end of cannula 102. A spring connector 104 is also stainless steel and is mounted on the proximal end of cannula 102 such that spring connector 104 is electrically connected to electrode tip 116 via cannula 102. A connector 106, having a face 107, a threaded portion 108, an inner portion 105, wings 109, and a ratchet post 110, surrounds and is rigidly connected to cannula 102. Lock-bumps 103 are located on face 107 of connector 106. Connector 106 is made out of a non-conductive material (such as plastic) and is used to connect instrument assembly 100 to a control handle (not shown). A locking sleeve grip 112 slides longitudinally on a ratchet post 110, which is a portion of connector 106, and is selectively positionable on ratchet post 110 by engaging detents or serrations 110c on ratchet post 110. A protective sleeve 114 is connected to locking sleeve grip 112 such that protective sleeve 114 may be extended distally to cover electrode tip 116 or retracted proximally to expose electrode tip 116 as the locking sleeve grip is urged distally or proximally. Protective sleeve 114 is shown in an extended position in FIG. 2 as opposed to the retracted position shown in FIG. 1. Holes 118 are located through sleeve 114 at its distal end for side venting of suction.

FIGS. 3a–3c show a cutaway view exposing the locking device responsible for the locking process. FIG. 3a shows a cutaway view exposing the locking device in the retracted position and FIG. 3b shows a cutaway view exposing the locking device in the extended but unlocked position. FIG. 3c shows a cutaway view exposing the locking device in the extended position and rotated 90° relative to that position shown in FIG. 3b so as to depict the locking device in the locked position.

As shown in these illustrations, the connector 106 consists of a threaded portion 108 (shown in FIG. 2) responsible for attachment of the electrode assembly to a control handle (not shown) and a ratchet post 110 extending from connector 106 over which the locking sleeve grip 112 rides. Ratchet post 110 has serrated portions 110c and 110d over which a metal C-ring 113 contained within the locking sleeve grip 112 rides.

Figure 4:
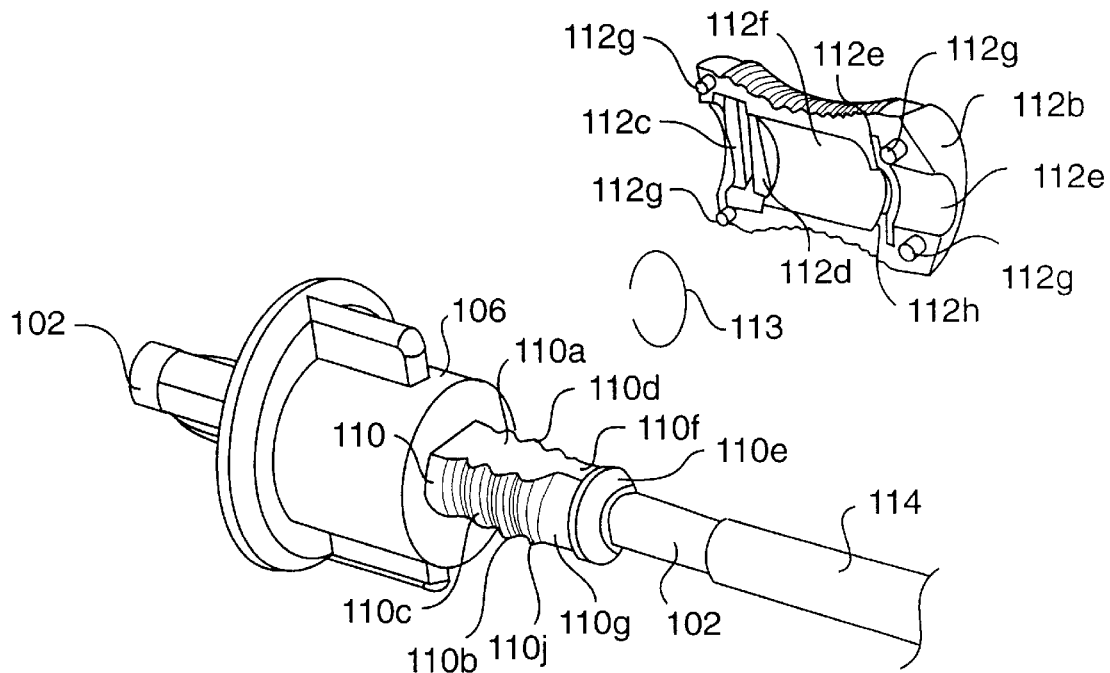
FIG. 4 is an exploded view of the same embodiment of the locking device of FIG. 3c in the locking position.
Figure 5:
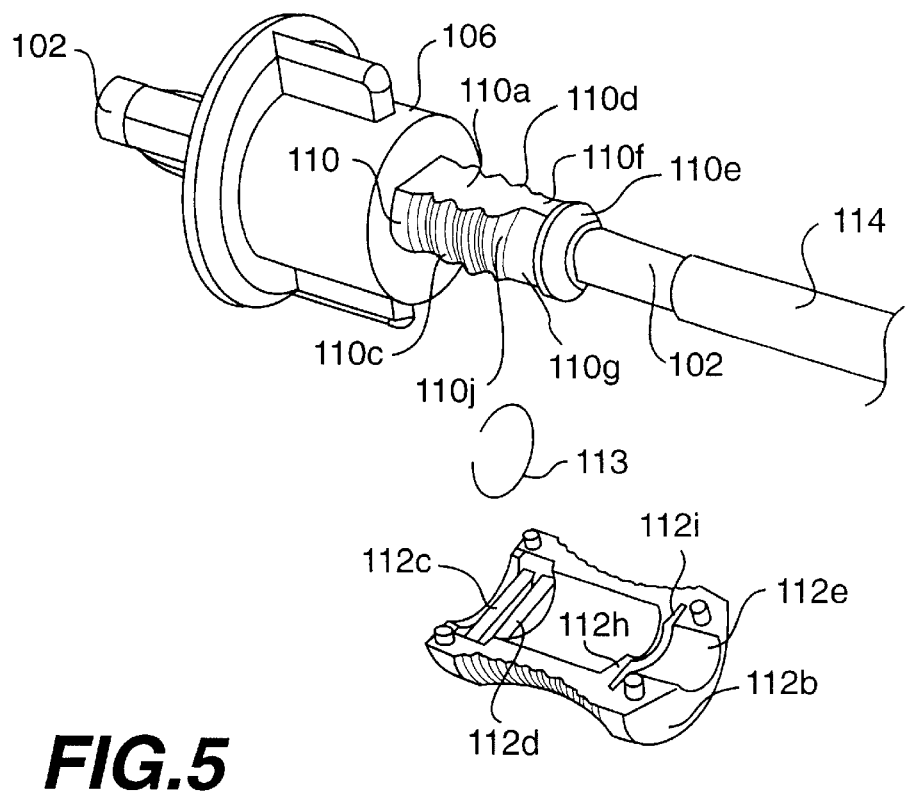
FIG. 5 is an exploded view of the same embodiment of the locking device of FIG. 3b in the extended but unlocked position.
Figure 6:
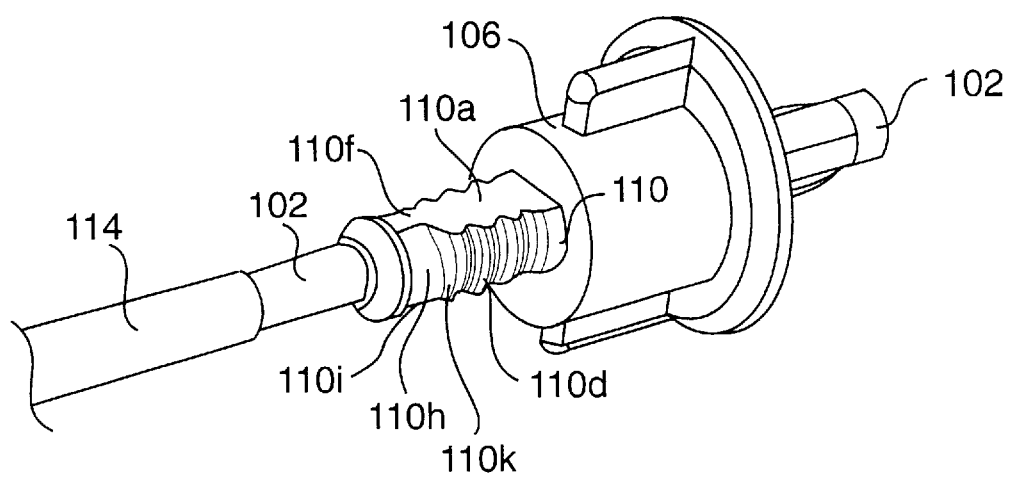
FIG. 6 is a mirror view of the portion of the locking device shown in FIGS. 4 and 5, showing elements not visible in FIGS. 4 and 5.

FIG. 4 is an exploded view of the locking device in the locked position and FIG. 5 is an exploded view of the locking device in the unlocked position. FIG. 6 is a mirror view of part of the locking device shown in FIGS. 4 and 5, thus showing elements not visible in FIGS. 4 and 5. In these figures, connector 106 is shown having ratchet post 110 extending longitudinally therefrom. Ratchet post 110 includes two serrated portions, 110c and 110d, diametrically opposed to each other, two flat portions, 110a and 110b, diametrically opposed to each other with 110b on the underside of ratchet post 110 (as shown in the figures), two ramp portions 110g and 110h, diametrically opposed to each other, and a nose portion 110e. A flat section 110f of flat portion 110a extends longitudinally toward nose portion 110e. Similarly a flat section 110i extends longitudinally toward nose portion 110e from flat portion 110b, located on the underside of ratchet post 110 in the figures. Shoulders 110j and 110k are located where serrated portions 110c and 110d meet ramp portions 110g and 110h.

C-ring 113 is made from spring steel and fits over ratchet post 110. The inside diameter of C-ring 113 is such that it must expand to slide longitudinally over the serrations on serrated portions 110c and 110d.

Only one half of sleeve grip 112 (that half being 112b) is shown in the figures, for clarity. Sleeve grip half 112a is similar in design to sleeve grip half 112b which has mating posts 112g, except that sleeve grip half 112a has mating holes to receive mating posts 112g. It is noted that the descriptions and functions of the various portions of sleeve grip half 112b, which follow, are also applicable to sleeve grip half 112a, which is not shown in detail, but which forms sleeve grip 112 together with sleeve grip half 112b.

Sleeve grip half 112b is shown having an axial hole at the distal end for gripping the proximal end of sleeve 114 and a larger axial hole 112f which has a major diameter large enough to clear serrated portions 110c and 110d of ratchet post 110 when sleeve grip half 112b is assembled with sleeve grip half 112a, thereby enclosing ratchet post 110. Posts 112c and 112d are positioned at the proximal end of sleeve grip half 112b and C-ring 113 is loosely trapped between posts 112c and 112d when the device is assembled.

When sleeve grip 112 is assembled and in the extended (distal) position, the distal face of post 112d abuts the proximal face of nose portion 110e, thus preventing further distal travel of sleeve grip 112. When sleeve grip 112 is in the unlocked position, as shown in FIG. 5, sleeve grip 112 may be urged proximally and posts 112c and 112d will glide over flat section 110i (located underneath ratchet post 110, diametrically opposite from flat section 110f) onto flat portion 110b (located underneath ratchet post 110, diametrically opposite from flat portion 110a). As sleeve grip 112 is urged proximally, C-ring 113 expands and contracts as it passes over each serration on serrated portions 110c and 110d, thus providing a detent type mechanism which will retain sleeve grip 112 in any of several longitudinal positions, thereby allowing differing amounts of electrode 116 to be exposed beyond sleeve 114.

Sleeve grip 112 may be locked in the extended position by rotating sleeve grip 112 ninety degrees, as shown in FIG. 4. As sleeve grip 112 is rotated as such, posts 112c and 112d ride on ramp portion 110h (as the posts located on sleeve grip half 112a ride on ramp portion 110g), and the proximal face of post 112c abuts shoulder 110k, thus preventing proximal movement of sleeve grip 112. Sleeve grip 112 is prevented from turning further than ninety degrees (position shown in FIG. 4) because posts 112c and 112d contact the edge of ramp portion 110h. Sleeve grip 112 is then prevented from turning more than ninety degrees in the unlocked direction (position shown in FIG. 5) by the contact of posts 112c and 112d with the edge of flat section 110i.

In further explanation, it is noted that, when sleeve grip halves 112a and 112b are assembled, the distance between posts 112c and 112d on sleeve grip half 112b and the posts on sleeve grip half 112a is greater than the diameter of ratchet post 110 as measured across flat portions 110a and 110b, but it is less than the diameter of ratchet post 110 as measured across serrated portions 110c and 110d. Thus, sleeve grip 112 can only slide proximally when it is in the unlocked position, shown in FIG. 5, such that posts 112c and 112d are aligned with flat portion 110b (and likewise the posts on sleeve grip half 112a are aligned with flat portion 110a).

It should further be noted that sleeve 114 is prevented from sliding proximally within sleeve grip 112 by wall 112h, as shown in FIGS. 4 and 5. Also, slot 112i is provided for receiving a sleeve securing means such as an E-ring for securing sleeve 114 in sleeve grip 112.

Also, the post and sleeve grip could be shaped in any number of alternate configurations in order to allow for lateral movement of the sleeve grip with respect to said post only when said post is in a particular orientation. For example, this could also be accomplished by providing a J-shaped channel in the post, having a long longitudinally portion and a short circumferential portion, and a corresponding pin in the sleeve grip such that the pin rides in the channel, wherein locking is provided by rotating the sleeve portion such that the pin moves into the circumferential portion of the channel.

Although the invention has been described in considerable detail with respect to the preferred embodiments thereof, variations and modifications will be apparent to those skilled in the art without departing from the spirit and scope of the invention as set forth in the claims.

I claim:

1. A locking device for use on an electrode assembly comprising a connector for connecting said electrode assembly to an electrosurgical control handle, an elongated electrode, having a proximal end and a distal end, extending through said connector such that said connector is located at the proximal end of said elongated electrode, and a protective sleeve movable from a proximal or retracted position wherein said electrode is exposed to an distal or extended position wherein said electrode is covered, said locking device comprising:

a locking post extending longitudinally from said connector and surrounding said elongated electrode and including a locking portion; and a rotatable sleeve grip connected to the proximal end of said sleeve, said sleeve grip surrounding said post for longitudinal movement therealong and being rotatable between an unlocked position wherein said sleeve grip is out of engagement with said locking portion of said post and said sleeve grip is movable longitudinally with respect to said post and a locked position wherein said sleeve grip engages said locking portion of said post and said sleeve grin is restricted from moving longitudinally with respect to said post.

2. A locking device as in claim 1, wherein:

said post has a proximal portion having a major diameter and a minor diameter and a distal portion wherein a lesser circumferential portion of said post has said major diameter, and a radial shoulder portion between said proximal portion and said distal portion and comprising said locking portion; and said sleeve grip has an axial hole therethrough wherein a portion of said axial hole has a major diameter slightly larger than said major diameter of said proximal portion of said post and having a minor diameter slightly larger than said minor diameter of said proximal portion of said post such that said sleeve grip is in said unlocked position wherein said sleeve grip is moveable longitudinally with respect to said post only when said major an minor diameters of said portion of said axial hole of said sleeve grip and said major and minor diameters of said proximal portion of said post are aligned, and said sleeve grip is rotatable to said locked position when said sleeve grip is moved to said extended position and rotated with respect to said post such that said portion of said axial hole of said sleeve grip having said minor diameter is aligned with said major diameter of said post, therein being prevented from moving proximally over said post by said shoulder portion of said post.

3. A locking device as in claim 2, wherein said minor diameter of said proximal portion is defined by two diametrically opposed flat surfaces, and said minor diameter of said axial hole in said proximal end of said sleeve grip is defined by posts which cooperate with said flat surfaces to allow said longitudinal movement of said sleeve grip with respect to said post.

4. A locking device as in claim 2, further comprising a detent means, in engagement with said sleeve grip and selectively engageable with said post, for providing selective positioning of said sleeve grip along said post.

5. A locking device as in claim 4, wherein said detent means comprises a C-ring, wherein said major diameter of said proximal portion of said post comprises circumferential, longitudinally spaced serrations, said C-ring surrounds said post and is engaged by a portion of said sleeve grip such that said C-ring expands to engage each of said serrations as said sleeve grip is moved longitudinally with respect to said post.

6. A locking device as in claim 2, further comprising a nose portion located at the distal end of said post for engaging a portion of said sleeve grip when said sleeve grip is in the extended position, therein preventing said sleeve grip from moving distally beyond said extended position.

7. A locking device as claimed in claim 1 wherein said sleeve grip is moveable along a longitudinal path between end positions, wherein said locking portion of said locking post is located at one end of said positions and wherein said locking post includes means for preventing rotation of said rotatable sleeve grip at positions along said longitudinal path other than said one end position.

* * * * *